(12) United States Patent
Shih et al.

(10) Patent No.: US 6,895,073 B2
(45) Date of Patent: May 17, 2005

(54) HIGH-SPEED X-RAY INSPECTION APPARATUS AND METHOD

(75) Inventors: Ang Shih, San Jose, CA (US); S. Jeffrey Rosner, Palo Alto, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 49 days.

(21) Appl. No.: 10/302,536

(22) Filed: Nov. 22, 2002

(65) Prior Publication Data

US 2004/0101109 A1 May 27, 2004

(51) Int. Cl.⁷ .................. G01N 23/04; G06K 9/03; G06K 9/68
(52) U.S. Cl. .............. 378/58; 378/98.12; 378/197; 378/207; 382/149; 382/150; 382/219; 382/220
(58) Field of Search .............. 378/21–27, 57, 378/58, 98.11, 98.12, 195–197, 207; 382/132, 149, 150, 219, 220

(56) References Cited

U.S. PATENT DOCUMENTS

| | | | |
|---|---|---|---|
| 4,415,980 A | | 11/1983 | Buchanan |
| 4,694,479 A | | 9/1987 | Bacskai et al. |
| 4,926,452 A | * | 5/1990 | Baker et al. .................. 378/22 |
| 5,463,667 A | * | 10/1995 | Ichinose et al. .............. 378/58 |
| 6,072,855 A | * | 6/2000 | Arakawa .................. 378/98.11 |
| 6,335,960 B2 | * | 1/2002 | Knigge et al. ................. 378/57 |
| 6,483,890 B1 | * | 11/2002 | Malamud ..................... 378/22 |
| 6,501,822 B2 | * | 12/2002 | Roder .......................... 378/22 |
| 6,574,303 B2 | * | 6/2003 | Sawada ........................ 378/58 |
| 6,656,648 B2 | * | 12/2003 | Inoue ......................... 382/149 |

FOREIGN PATENT DOCUMENTS

| | | |
|---|---|---|
| DE | 267 568 | 12/1987 |
| EP | 0 407 685 | 2/1990 |
| EP | 1 046 904 | 10/2000 |

OTHER PUBLICATIONS

Hanke, R.F. et al., "Automated 3D X–Ray Inspection of Fine Pitch PCB's", IEEE/CHMT Intl. Electronics Manufacturing Technology Symposium, Sept. 28, 1992, pp. 187–190.

* cited by examiner

Primary Examiner—Allen C. Ho

(57) ABSTRACT

An apparatus and method for inspecting parts. The apparatus includes an x-ray source for illuminating a part from a plurality of locations with respect to the part and an imaging detector for forming a plurality of measured x-ray images of the part, one such measured x-ray image corresponding to each of the illumination locations. A controller compares each of the measured x-ray images with a corresponding calibration image. The controller provides a defective part indication if one of the measured x-ray images differs from the corresponding calibration image by more than a threshold value in part of the measured x-ray image. The controller localizes defects on the part by comparing two or more of the measured x-ray images with two or more corresponding calibration images. The calibration images can be constructed from measured images of defect free parts.

4 Claims, 1 Drawing Sheet

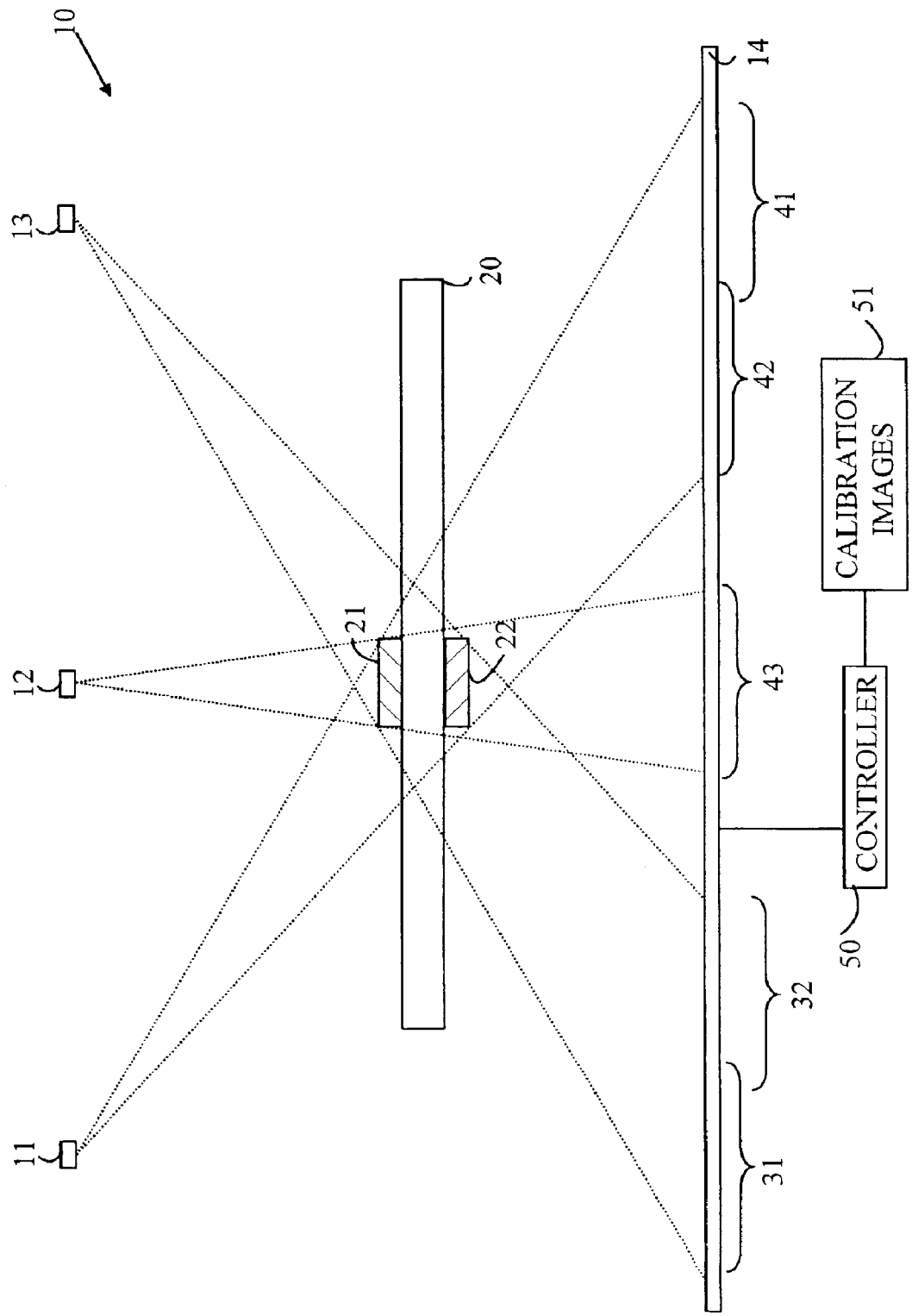

HIGH-SPEED X-RAY INSPECTION APPARATUS AND METHOD

FIELD OF THE INVENTION

The present invention relates to x-ray inspection systems.

BACKGROUND OF THE INVENTION

In many industries x-ray inspection is being used routinely for inspection of products in the manufacturing environment. The simplest form of x-ray imaging is transmission imaging. In x-ray transmission imaging, illumination is projected through an object and the imaging signal results from a subtractive process, i.e.; what is imaged is the far field of the illumination minus any of the illumination that was absorbed, reflected or scattered. Such images can be quickly generated with relatively inexpensive equipment. However, detail needed to detect a flaw in a part can be obscured in such images when the defective feature is masked by an area of highly absorbing material that overlaps the defective feature in the image. For example, the solder joints on printed circuit boards are often examined via x-ray inspection to detect defective solder joints. Unfortunately, a large solder joint on one surface of the board can interfere with the image of a smaller joint on the other side of the board if the larger joint shadows the smaller joint.

The shadowing problem can be substantially reduced when three-dimensional x-ray images are formed of the object. In essence, the object is divided into thin slices that are individually examined. Hence, one object that obscures another object in one slice will not obscure the other object in another slice. Such three-dimensional images are often used in medical diagnostic work.

Unfortunately, the high cost of this equipment and its relatively low throughput has inhibited the use of three-dimensional scanners for such high volume applications as parts inspection. Three-dimensional scanners such as CT scanners require that a large number of views of the object be taken from a large number of different angles. This data must then be combined to provide the three-dimensional image in which the part is modeled as a three dimensional array of volume elements called voxels. The three-dimensional image must then be analyzed to detect flaws in the part.

In a typical CT scanner, the x-ray source and the detector are fixed relative to one another and are rotated around the object. The time needed to generate a three-dimensional image with such a system makes such systems impractical in high-speed part scanning applications. In addition, the cost of the hardware and the floor space required further discourage the use of such systems in industrial inspection applications. Finally, the computational costs of the analysis of the three-dimensional images also increases the cost of such systems.

Broadly, it is the object of the present invention to provide an improved x-ray inspection apparatus and method.

This and other objects of the present invention will become apparent to those skilled in the art from the following detailed description of the invention and the accompanying drawings.

SUMMARY OF THE INVENTION

The present invention is an apparatus and method for inspecting parts. The apparatus includes an x-ray source for illuminating a part from a plurality of locations with respect to the part and an imaging detector for forming a plurality of measured x-ray images of the part, one such measured x-ray image corresponding to each of the illumination locations. A controller compares each of the measured x-ray images with a corresponding calibration image. The controller provides a defective part indication if one of the measured x-ray images differs from the corresponding calibration image by more than a threshold value in part of the measured x-ray image. The controller localizes defects on the part by comparing two of the measured x-ray images with two corresponding calibration images. The calibration images can be constructed from measured images of defect-free parts. Embodiments in which a running average of measured images of defect-free parts is used to construct the calibration images can also be practiced.

BRIEF DESCRIPTION OF THE DRAWING

The drawing is a cross-sectional view of one embodiment of an image inspection system 10 according to the present invention operating on a part 20 having features on the top and bottom surfaces thereof.

DETAILED DESCRIPTION OF THE PREFERRED EMBODIMENTS OF THE INVENTION

The manner in which the present invention provides its advantages can be more easily understood with reference to the drawing, which is a cross-sectional view of one embodiment of an image inspection system 10 according to the present invention operating on a part 20 having features on the top and bottom surfaces thereof. Inspection system 10 has two or more x-ray sources, by way of example shown here are three sources 11–13 and an x-ray detector 14 that is preferably a two-dimensional array of x-ray detectors for forming an image of part 20. To simplify the following discussion, it will be assumed that there are only two features of interest on part 20, feature 21 on the top surface and feature 22 on the bottom surface. Consider the image formed by x-ray source 13 on detector 14. The image will have two slightly overlapping shadows at 31 and 32 corresponding to the absorption of the x-rays by features 21 and 22, respectively. Similarly, the image formed by x-ray source 11 will have two slightly overlapping shadows at 41 and 42 corresponding to the absorption of the x-rays by features 21 and 22, respectively. The image formed by x-ray source 12, on the other hand, will have one shadow at location 43.

Consider the case in which feature 21 has a small defect. For example, assume that a part of the feature is missing. The defect will be more visible in the images formed by x-ray sources 11 and 13 than by x-ray source 12. In particular, a portion of the shadows at 31 and 41 will be missing. In contrast, the shadow at 43 will remain the same size with a change in the density of the shadow in the region of the defect. If the x-ray absorption of feature 22 is significantly greater than that of feature 21, this change in density can be masked.

The inspection process of the present invention can be divided into two phases. In the first phase, the part is imaged and a determination is made as to whether or not the part is defective. In the second phase, the fault is localized on the part so that the fault can be repaired, if possible.

The first phase is carried out by comparing a plurality of images of the part with calibration images. Each image is formed by utilizing an x-ray source that is at a different position relative to the part. In the exemplary system shown in FIG. 1, three images would be taken corresponding to x-ray sources 11–13. For each measured image, controller 50 accesses a calibration image that is stored in memory 51. Controller 50 compares the measured image to the calibration image. If the measured image differs substantially from the calibration image at a significant location in any of the measured images, the part is assumed to be defective.

The calibration images represent the expected image from a good part taken with the corresponding x-ray source. The calibration images can be generated by a number of different methods. For example, the calibration image can be computed from the drawings of the part that are stored in a computer-aided-design representation of the part. The calibration image can also be generated by forming images of a number of parts that are known to be good using the corresponding x-ray source.

It should be noted that the calibration images can be periodically updated to correct the images for drift in the manufacturing process. In this case, the calibration images can be generated by forming the weighted sum of the previously scanned parts that are known to be defect free. The calibration images can include time-weighting that emphasizes the most recent parts to accurately compensate for tolerable drifts in the manufacturing process. These can be continuously updated as good product is identified. The variation in these calibration images as a function of time can be useful as a process monitor to quantitatively identify drift in the manufacturing process.

The comparison of the measured and calibration images can be carried out via a number of different algorithms. Any algorithm that measures the local deviations of the measured image from the corresponding calibration image can be utilized. For example, a difference image can be formed after normalizing the measured image. In the simplest method, the average mean-squared-amplitude of the pixels in the difference image can be used to determine if the measured image differs significantly from the corresponding calibration image. However, this simple method over emphasizes regions in which no defects are expected. This problem can be overcome by utilizing a weighting function that weights different areas of the different image according to the likelihood of a fault being present.

The above-described comparison method assumes that the measured image and calibration are properly registered with respect to one another before the images are subtracted from each other. Since the part can be moved into scanning position by a mechanical positioning mechanism in most cases, the preferred embodiment of the present invention preprocesses the measured image to correct for positioning errors. The position errors can be corrected by a suitable image processing routine that shifts the relative position of the calibration and measured images and/or performs a specific distortion of one of the images prior to the subtraction. Such image matching algorithms are known to the art, and hence, will not be discussed in detail here. It should be noted that images of flat objects such as printed circuit boards require less correction than three-dimensional objects having a significant height.

The differences between the measured image and the calibration image represent variation in the product. Consider the inspection of printed circuit boards and assume that the calibration image is subtracted from the measured image. A missing part gives rise to a large area having an extreme negative value. An extra part gives rise to a large area having an extreme positive value. Insufficient solder at a bonding part gives rise to a small or medium area having an extreme negative value. Excessive solder gives rise to a similar area having an extreme positive value, and so on.

If a defect is visible in at least two of the views, the location of the defect can be determined on the part. The location of the defect in one view defines a cone having its apex at the x-ray source used to take the image and its base defined by the defect area in the image. The intersection of that cone with the part defines a set of locations in which the defect exists. If the part is thin enough, this may be sufficient to provide sufficient localization. However, in general, more information is needed. The defect in the second view provides that information by defining a second cone having its apex on the corresponding x-ray source and a base determined by the defect area in the second image. The intersection of these two cones with the part defines a smaller volume in which the defect is localized. If more views in which the defect is seen are available, the defect can be localized still further.

The minimum number of views that will provide both defect detection and localization is two. However, as noted above, a defect may be masked in one or more views. Hence, systems with a larger number of views may be advantageous.

It should be noted that the present invention can detect defects and localize the detected defects without having to generate a three-dimensional representation of the part. Hence, the computational workload and inspection are substantially less than systems that depend on some form of three-dimensional reconstruction. It should also be noted that the present invention requires far fewer images than systems based on three-dimensional image reconstruction.

The above-described embodiments of the present invention utilize a number of separate x-ray sources. However, systems in which a single movable x-ray source is used can also be constructed. In addition, scanning x-ray sources in which an electron beam is moved over a large target can also be utilized without departing from the teachings of the present invention. If the imaging detector is sufficiently large, a single x-ray source can be utilized to take multiple images as the part moves between the imaging source and imaging detector.

The above-described embodiments of the present invention utilize a single imaging detector. However, embodiments having multiple image detectors can also be practiced. Embodiments in which there is one imaging detector for each x-ray source location are particularly useful. In such embodiments, the individual imaging detectors can be oriented such that the x-rays strike the imaging detectors at angles that are more nearly normal to the direction of the x-rays.

Various modifications to the present invention will become apparent to those skilled in the art from the foregoing description and accompanying drawings. Accordingly, the present invention is to be limited solely by the scope of the following claims.

What is claimed is:

1. An apparatus comprising:
   an x-ray source for illuminating a part from a plurality of locations with respect to said part;
   an imaging detector for forming a plurality of measured x-ray images of said part, one such measured x-ray image corresponding to each of said illumination locations; and
   a controller for comparing each of said measured x-ray images with a corresponding calibration image, said controller providing a defective part indication if one of said measured x-ray images differs from said corresponding calibration image by more than a threshold value in part of said measured x-ray image, and wherein said controller forms a weighted difference image from each of said measured images and said corresponding calibration image, said weighted difference image utilizing a weighting function that varies over said measured image and said corresponding calibration image.

2. An apparatus comprising:

an x-ray source for illuminating a part from a plurality of locations with respect to said part;

an imaging detector for forming a plurality of measured x-ray images of said part, one such measured x-ray image corresponding to each of said illumination locations; and a controller for comparing each of said measured x-ray images with a corresponding calibration image, said controller providing a defective part indication if one of said measured x-ray images differs from said corresponding calibration image by more than a threshold value in part of said measured x-ray image, wherein one of said calibration images comprises data from a plurality of said measured images from different examples of said part.

3. A method of screening pans for defects, said method comprising:

forming a first measured x-ray image of one of said parts with an x-ray source in a first location relative to said part;

forming a second measured x-ray image of that part with an x-ray source in a second location relative to that part, said first location being different from said second location; and providing a defective indication for said part if said first measured x-ray image differs from said first calibration image by more tan a first threshold value in part of said first measured x-ray image or if said second measured x-ray image differs from said second calibration image by more than a second threshold value in part of said second measured x-ray image, and wherein a weighted difference image is used to determine if said first measured x-ray image differs from said first calibration image.

4. A method of screening parts for defects, said method comprising:

forming a first measured x-ray image of one of said parts with an x-ray source in a first location relative to said part;

forming a second measured x-ray image of that part with an x-ray source in a second location relative to that part, said first location being different from said second location; and providing a defective indication for said part if said first measured x-ray image differs from said first calibration image by more than a first threshold value in part of said first measured x-ray image or if said second measured x-ray image differs from said second calibration image by more than a second threshold value in part of said second measured x-ray image, and wherein one of said calibration images comprises data from a plurality of said measured images from different ones of said parts.

* * * * *

UNITED STATES PATENT AND TRADEMARK OFFICE
CERTIFICATE OF CORRECTION

PATENT NO.   : 6,895,073 B2
DATED        : May 17, 2005
INVENTOR(S)  : Shih et al.

It is certified that error appears in the above-identified patent and that said Letters Patent is hereby corrected as shown below:

Column 5,
Line 25, delete "pans" and insert -- parts --.

Column 6,
Line 3, delete "tan" and insert -- than --.

Signed and Sealed this

Fourteenth Day of February, 2006

JON W. DUDAS
*Director of the United States Patent and Trademark Office*